(12) United States Patent
Zamierowski

(10) Patent No.: US 9,456,930 B2
(45) Date of Patent: Oct. 4, 2016

(54) TOPICAL VACUUM-PRESS SURGICAL INCISIONAL DRESSINGS, SURGICAL ADJUNCTS, HYBRIDS AND COMPOSITES

(71) Applicant: KCI Licensing, Inc., San Antonio, TX (US)

(72) Inventor: David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 380 days.

(21) Appl. No.: 14/217,219

(22) Filed: Mar. 17, 2014

(65) Prior Publication Data

US 2014/0276495 A1    Sep. 18, 2014

Related U.S. Application Data

(60) Provisional application No. 61/800,224, filed on Mar. 15, 2013.

(51) Int. Cl.
*A61F 13/02* (2006.01)
*A61M 1/00* (2006.01)
*A61F 13/00* (2006.01)

(52) U.S. Cl.
CPC ..... *A61F 13/0216* (2013.01); *A61F 13/00068* (2013.01); *A61M 1/0088* (2013.01)

(58) Field of Classification Search
CPC .................. A61F 13/0216; A61F 13/00068; A61M 1/0088
See application file for complete search history.

(56) References Cited

U.S. PATENT DOCUMENTS

| 221,427 | A | 11/1879 | Sherman |
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| AU | 550575 | 8/1982 |
| AU | 745271 | 12/2002 |

(Continued)

OTHER PUBLICATIONS

"Extended European Search Report", European Patent Application No. 14763938.9, Mar. 24, 2016, pp. 1-7.

(Continued)

*Primary Examiner* — Leslie Deak
*Assistant Examiner* — Kai Weng
(74) *Attorney, Agent, or Firm* — Law Office of Mark Brown, LLC; Mark E. Brown

(57) ABSTRACT

A negative pressure wound therapy (NPWT) dressing includes a wick configured for placement over an incision. A transfer assembly includes a compressible, porous core with a permeable cover placed over the core. The transfer assembly is positioned on the wick in fluidic contact and is covered by a dressing cover, which is configured for adhesive attachment to the patient around the incision. A drain slip including a proximal end configured for placement in the incision extends through the wick and the transfer assembly and is configured for connection to a negative pressure source. A NPWT method includes steps of draining a closed incision using negative pressure applied to a drain slip.

20 Claims, 1 Drawing Sheet

(56) References Cited

U.S. PATENT DOCUMENTS

| | | |
|---|---|---|
| 2,910,763 A | 11/1959 | Lauterbach |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,248,232 A | 2/1981 | Engelbrecht et al. |
| 4,250,882 A * | 2/1981 | Adair ............... A61F 13/00068 128/888 |
| 4,256,109 A | 3/1981 | Nichols |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,045,075 A | 9/1991 | Ersek |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Kubein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle et al. |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Tumey |
| 6,493,568 B1 | 12/2002 | Bell et al. |
| 6,500,209 B1 | 12/2002 | Kolb |
| 6,503,281 B1 | 1/2003 | Mallory |
| 6,540,705 B2 | 4/2003 | Norstrem et al. |
| 6,553,998 B2 | 4/2003 | Heaton et al. |
| 6,589,285 B2 | 7/2003 | Penenberg |

(56) References Cited

U.S. PATENT DOCUMENTS

| | | |
|---|---|---|
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |
| 6,695,823 B1 | 2/2004 | Lina et al. |
| 6,695,824 B2 | 2/2004 | Howard et al. |
| 6,726,706 B2 | 4/2004 | Dominguez |
| 6,752,794 B2 | 6/2004 | Lockwood et al. |
| 6,764,462 B2 | 7/2004 | Risk et al. |
| 6,800,074 B2 | 10/2004 | Henley et al. |
| 6,814,079 B2 | 11/2004 | Heaton et al. |
| 6,824,533 B2 | 11/2004 | Risk et al. |
| 6,828,468 B2 | 12/2004 | Ansmann et al. |
| 6,856,821 B2 | 2/2005 | Johnson |
| 6,860,903 B2 | 3/2005 | Mears et al. |
| 6,936,037 B2 | 8/2005 | Bubb |
| 6,951,553 B2 | 10/2005 | Bubb et al. |
| 6,953,480 B2 | 10/2005 | Mears et al. |
| 6,991,643 B2 | 1/2006 | Saadat |
| 7,070,584 B2 | 7/2006 | Johnson et al. |
| 7,105,021 B2 | 9/2006 | Edens et al. |
| 7,108,683 B2 | 9/2006 | Zamierowski |
| 7,381,211 B2 | 6/2008 | Zamierowski |
| 7,645,269 B2 | 1/2010 | Zamierowski |
| 7,976,519 B2 | 7/2011 | Bubb et al. |
| 8,162,907 B2 | 4/2012 | Heagle |
| 8,366,693 B2 | 2/2013 | Hu et al. |
| 8,394,081 B2 | 3/2013 | Locke et al. |
| 2002/0022861 A1 | 2/2002 | Jacobs et al. |
| 2002/0029063 A1 | 3/2002 | Wittmann |
| 2002/0143286 A1 | 10/2002 | Tumey |
| 2004/0006319 A1 | 1/2004 | Lina et al. |
| 2005/0043818 A1 | 2/2005 | Bellon et al. |
| 2006/0079852 A1 | 4/2006 | Bubb et al. |
| 2008/0208171 A1* | 8/2008 | Argenta ............ A61M 1/0088 604/540 |
| 2009/0227969 A1 | 9/2009 | Jaeb et al. |
| 2011/0092927 A1 | 4/2011 | Wilkes et al. |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2195255 | 4/1988 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2004/060148 | 7/2004 |
| WO | 2011008360 | 1/2011 |

OTHER PUBLICATIONS

"International Search Report and Written Opinion", PCT/US2014/030860, Sep. 8, 2014, pp. 1-12.

Morykwas, et al., "Vacuum-Assisted Closure: A new Method for Wound Control and Treatment: Animal Studies and Basic Foundation", Annals of Plastic Surgery, vol. 38, No. 6, 1997, 553-562.

Norman, et al., "Methods for Fabrication of Nanoscale Topography for Tissue Engineering Scaffolds", Annals of Biomedical Engineering, vol. 34, No. 1, Jan. 2006, 89-101.

Orringer, et al., "Management of Wounds in Patients with Complex Enterocutaneous Fistulas", Surgery, Gynecology & Obstetrics, vol. 165, Jul. 1987, 79-80.

Pailler-Mattei, et al., "Study of Adhesion Forces and Mechanical Properties of Human Skin in vivo", J. Adhesion Sci. Technol., vol. 18, No. 15-16, 2004, 1739-1758.

Pfister, et al., "Neural Engineering to Produce In Vitro Nerve Constructs and Neurointerface", Neurosurgery: www.neurosurgery-online.com, 2007, 137-142.

Poritz, et al., "Percutaneous Drainge and Ileocolectomy for Spontaneus Intraabdominal Abscess in Chrohn's Disease", J. Gast. Surg., vol. 11, Jan. 19, 2007, 204-207.

Puyana, "Resuscitation of Hypovolemic Shock", Textbook of Critical Care, 5th Ed., Ch. 229, 2005, 1933-1943.

Reckard, et al., "Management of Intraabdominal Hypertension by Percutaneous Catheter Drainage", JVIR, vol. 16, No. 7, Jul. 2005, 1019-1021.

Robledo-Ogazon, et al., "Using the Vacuum Assisted Closure System VAC in the Treatment of Infected Surgical Wounds. Clinical Experience", madigraphic Artemisa, vol. 74, No. 2, Mar.-Apr. 2006, 107-113.

Sachlos, et al., "Making Tissue Engineering Scaffolds Work. Review on the Application of Solid Freeform Fabrication Technology to the Production of Tissue Engineering Scaffolds", European Cells and Materials, vol. 5, 2003, 29-40.

Safronov, "Vacuum Therapy of Trophic Ulcers of the Lower Leg with Simultaneous Autoplasty of the Skin", Ministry of Public Health of the USSR, 1967, 1-50.

Saxena, et al., "Vacuum-Assisted Closure: Microdeformations of Wounds and Cell Proliferation", Plast Reconstr Surg., 114(5), Oct. 2004, 1086-1096.

Schein, et al., "The 'sandwich technique' Management of the Open Abdomen", Br. J. Surg., vol. 73, May 1986, 369-370.

Segvich, et al., "Uniform Deposition of Protein Incorporated Mineral Layer on Three-Dimensional Porous Polymer Scaffolds", Journal of Biomedical Materials Research Part B: Applied Biomaterials 84B(2): <http://hdl.handle.net/2027.42/57926>, May 8, 2007, 340-349.

Sherck, et al., "Covering the "Open Abdomen": A Better Technique", The American Surgeon, vol. 64, Sep. 1998.

Shimko, et al., "Effect of Porosity on the Fluid Flow Characteristics and Mechanical Properties of Tantalum Scaffolds", Journal of Biomedical Materials Research, Part B, Applied Biomaterials, Sep. 24, 2004, 315-324.

Solovev, et al., "The Method of Treatment of Immature External Fistulas in the Upper Gastrointestinal Tract", S.M. Kirov Gorky State Medical Institute, 1987, 1-20.

Solovev, "Treatment and Prevention of Suture Failures After Gastric Resection", S.M. Kirov Gorky State Medical Institute, 1988, 1-55.

Stannard, et al., "Use of negative pressure wound therapy over clean, closed surgical incisions", International Wound Journal, 2012 vol. 9 (Suppl. 1), Aug. 2012, 32-39.

Svedman, "A Dressing Allowing Continuous Treatment of a Biosurface", IRCS Medical Science: Biomedical Technology; Clinical Medicine; Surgery and Transplantation, Jul. 1979, 221.

Svedman, et al., "A Dressing System Providing Fluid Supply and Suction Drainage Used for Continuous or Intermittent Irrigation", Annals of Plastic Surgery, vol. 17, No. 2, Aug. 1986, 125-133.

Svedman, "Irrigation Treatment of Leg Ulcers", The Lancet, vol. 322, Issue 8349, Sep. 3, 1983, 532-534.

Takahashi, et al., "Induction of Pluripotent Stem Cells from Mouse Embryonic and Adult Fibroblast Cultures by Defined Factors", Cell, vol. 126, Aug. 25, 2006, 663-676.

(56) References Cited

OTHER PUBLICATIONS

Tan, et al., "Inhibition of Osteocyte Apoptosis by Fluid Flow is Mediated by Nitric Oxide", Biochemical and Biophysical Research Communications, vol. 369, Issue 4, May 16, 2008, 1150-1154.
Tan, et al., "Osteocytes Subjected to Fluid Flow Inhibit Osteoclast Formation and Bone Resorption", Bone, vol. 4, Jul. 27, 2007, 745-751.
Tennant, "The Use of Hyperemia in the Postoperative Treatment of Lesions of the Extremities and Thorax", Jour. A.M.A., May 8, 1915, 1548-1549.
Timmenga, et al., "The Effect of Mechanical Stress on Healing Skin Wounds: An Experimental Study of Rabbits Using Tissue Expansion", British Journal of Plastic Surgery, vol. 44, 1991, 514-519.
Tribble, "An Improved Sump Drain-Irrigation Device of Simple Construction", Arch. Surg., vol. 105, Sep. 1972, 511-513.
Venturi, et al., "Mechanisms and CLinical Applications of the Vacuum-Assisted Closure (VAC) Device", Am. J. Clin. Dermatol., vol. 6 (3), 2005, 185-194.
Walsh, et al., "Directional Neurite Outgrowth Is Enhanced by Engineered Meningeal Cell-Coated Substrates", Tissue Engineering, vol. 11, No. 7/8, Mary Ann Liebert, Inc., 2005, 1085-1095.
Wilkes, et al., "3D Strain Measurement in Soft Tissue: Demonstration of a Novel Inverse Finite Element Model Algorithm on MicroCT Images of a Tissue Phantom Exposed to Negative Pressure Wound Therapy", Journal of the Mechanical Behavior of Biomedical Materials, Nov. 5, 2008, 1-16.
Yusupov, et al., "Active Wound Drainage", Vestnik Khirurgi, vol. 138, Issue 4, 1987, 42-46.
Zivadinovic, et al., "Vacuum Therapy in the Treatment of Peripheral Blood Vessels", Conference Papers of the 5th Timok Medical Days, Timok Medical Journal, Majdanpek, Copy and Certified Translation, 1986, 161-164.
Blackburn, II, MD, "Negative-Pressure Dressings as a bolster for Skin Grafts", Annals of Plastic Surgery, vol. 40, No. 5, May 1998, 453-457.
Boersma, et al., "Photogrammetric Wound Measurement with a Three-Camera Vision System", IAPRS, vol. 33, 2000.
Brabmamdam, et al., "Critical Care I", Surg. Forum Abstracts, vol. 207, No. 3S, Sep. 2008, S34-S35.
Brock, et al., "Temporary Closure of Open Abdominal Wounds: The Vacuum Pack", The Am. Surgeon Jan. 1995, 30-35.
Brody, et al., "Approaches to Heart Valve Tissue Engineering Scaffold Design", Journal of Biomedical Materials Research Part B: Applied Biomaterials, 2006, 16-43.
Burdette, et al., "Systemic Inflammatory Response Syndrome", eMedicine Critical Care; http://emedicine.medscape.com/article/168943-print, Apr. 16, 2007, 1-19.
Chariker, et al., "Effective Management of Incisional and Cutaneous Fistulae with Closed Suction Wound Drainage", Contemporary Surgery, vol. 34, Jun. 1989, 59-63.
Cheboksary, "Current Problems in Modern Clinical Surgery Interdepartmental Collection", Ministry of Higher and Secondary Education of the RSFSR I.N. Ulyanov Chuvash State University, May 21, 1986, 1-153.
Chinn, et al., "Closed Wound Suction Drainage", The Journal of Foot Surgery, vol. 1, No. 1, 1985, 76-81.
Culliford, et al., "A Novel Technique for Vacuum Assisted Closure Device Application in Noncontiguous Wounds", Journal of Plastic, Reconstructive and Aesthetic Surgery, 2006, 1-2.
Cunningham, "Development of in-vitro Model to Simulate Dermal Wound Bed Interaction with Granufoam and Gauze Dressing Under Sub Atmospheric Pressure", Micro CT Study-Test Cell Development, Report, Jul. 30, 2006, 1-19.
Dattilo, Jr., et al., "Medical Textiles: Application of an Absorbable Barbed Bi-directional Surgical Suture", Journal of Textile and Apparel, Technology and Management, vol. 2, Issue 2, Spring 2002, 1-5.
Davydov, et al., "Bacteriological and Cytological Assessment of Vacuum Therapy of Purulent Wounds", Vestnik Khirurgi, Oct. 1998, 48-52.
Davydov, et al., "Concepts for the Clinical-Biological Management of the Wound Process in the Treatment of Purulent Wounds by Means of Vacuum Therapy", Vestnik Khirurgi, Jul. 7, 1980, 132-136.
Davydov, et al., "Vacuum Therapy in the Treatment of Purulent Lactation Mastitis", Vestnik Khirurgi, May 14, 1986, 66-70.
Dee, "The Successful Management of a dehisced Surgical Wound with TNP Following Femoropopliteal Bypass", Journal of Wound Care, vol. 16, No. 1, Jan. 2007, 42-44.
Delalleau, et al., "Characterization of the Mechanical Properties of Skin by Inverse Analysis Combined with the Indentation Test", Journal of Biomechanics, vol. 39, 2006, 1603-1610.
Diridollou, et al., "In vivo Model of the Mechanical Properties of the Human Skin Under Suction", Skin Research and Technology, vol. 6, 2000, 214-221.
Dubick, et al., "Issues of Concern Regarding the Use of Hypertonic/Hyperoncotic Fluid Resuscitation of Hemorrahagic Hypotension", Shock, vol. 25, No. 4, 2006, 321-328.
Egnell Minor, "Addition to the User's Manual Concerning Overflow Protection", Industrigaton2, 461, 37 Trollhattan, Feb. 3, 1983, 2.
Egnell Minor, "Egnell Minor Instruction Book, 1st Edition, 300 7502", Feb. 1975, 1-24.
Fong, et al., "Initial Clinical Experience Using a Novel Ultraportable Negative Pressure Wound Therapy Device", Wounds, a Compendium of Clinical Research and Practice, vol. 22 Issue 9., Sep. 2010, 230-236.
Garner, et al., "Vacuum-Assisted Wound Closure Provides Early Fascial Reapproximation in Trauma Patients with Open Abdomens", The Am. Journ. Surg, vol. 182, 2001, 630-638.
Gemmiti, et al., "Fluid Flow Increases Type II Collagen Deposition and Tensile Mechanical Properties in Bioreactor-Grown Tissue-Engineered Cartilage", Tissue Engineering, vol. 12, No. 3, 2006, 469-479.
Grauhan, et al., "Prevention of Poststernotomy Wound Infections in Obese Patients by Negative Pressure Wound Therapy", The Journal of Thoracic and Cardiovascular Surgery, vol. 145, No. 5., May 2013, pp. 1387-1392.
Greer, et al., "The Use of Subatmospheric Pressure Dressing Therapy to Close Lymphocutaneous Fistulas of the Groin", British Journal of Plastic Surgery (2000), 53, 484-487.
Gupta, et al., "Guidelines for Managing Pressure Ulcers with Negative Pressure Wound Therapy", Supplement to Advances in Skin and Wound Care, vol. 17, Supp. 2, Nov. 2004, 1-16.
Herte, et al., "Comparative Wound Healing in Animal Subjects Using the Cuba System VS Conventional Surgical instruments", The American Society of Plastic and Reconstructive Surgeons, Nov. 1978, 1-19.
Jeschke, et al., "Development of New Reconstructive Techniques: Use of Integra in Combination with Fibrin Glue and Negative-Pressure Therapy fro Reconstruction of Acute and Chronic Wounds", Departments of General Surgery and Trauma and Reconstructive Surgery, University of Regensburg, Jan. 15, 2003, 525-530.
Jeter, et al., "Managing Draining Wounds and Fistulae: New and Established Methods", Chronic Wound Care: Health Management Publications, 1990, 240-246.
Johnson, "An Improved Technique for Skin Graft Placement Using a Suction Drain", Surgery, Gynecology & Obstetrics, vol. 159, Dec. 1984, 585-586.
Kaplan, et al., "Guidelines for the Management of the Open Abdomen", Supplement to Wounds, Oct. 2005, 1-26.
Khatyr, "Model of the Viscoelastic Behaviour of Skin in vivo and Study of Anisotropy", Skin Research and Technology, vol. 10, 2004, 96-103.
Kostyuchenok, et al., "Vacuum Treatment in the Surgical Management of Purulent Wounds", Vestnik Khirugi, Sep. 1986, 18-21.
Kuznetsov, et al., "Vacuum and Vacuum-Sorption Treatment of open Septic Wounds, Appendix B", II All-Union Conference on Wounds and Wound Infections: Presentation Abstracts Moscow, U.S.S.R., Oct. 29, 1986, 91-92.

(56) References Cited

OTHER PUBLICATIONS

Kwan, et al. "A Structural Model to Describe the Nonlinear stress-Strain Behavior for Parallel-Fibered Collagenous Tissues", Journal of Biomechanical Engineering, vol. 111, Nov. 1989, 361-363.
Lago, et al., "Neurobiological Assessment of Regenerative Electrodes for Bidirectional Interfacing Injured Peripheral Nerves", IEEE Transactions on Biomedical Engineering, vol. 54, No. 6, Jun. 2007, 1129-1137.
Laskin, "Minimally Invasive Total Knee Replacement Using a Mini-Mid Vastus Incision Technique and Results", Surgical Technology International, vol. 13, 2004, 231-238.
Latenser, et al., "A Pilot Study Comparing Percutaneous Decompression with Decompressive Laparotomy for Acute Abdominal Compartment Syndrome in Thermal Injury", Journal of Burn Care & Rehab., vol. 23, No. 3, May/Jun. 2002, 190-195.
Lavery, et al., "Emerging Concepts with VAC Therapy", Podiatry Today, vol. 20, Jul. 1, 2007, 1-6.
Letsou, M.D., et al., "Stimulation of Adenylate Cyclase Activity in Cultured Endothelial Cells Subjected to Cyclic Stretch", Journal of Cardiovascular Surgery, 31, 1990, 534-539.
Manwaring, et al., "Characterization of Rat Meningeal Cultures on Materials of Differing Surface Chemistry", Biomaterials, vol. 22, 2001.
Manwaring, et al., "Contact Guidance Induced Organization of Extracellular Matrix", Biomaterials, vol. 25, 2003, 3631-3638.
Masters, "Letter to the Editor", British Journal of Plastic Surgery, vol. 51(3), 1998; Elsevier Science/The British Association of Plastic Surgeons, UK, 267.
Mendez-Eastman, RN, "When Wounds Won't Heal", RN, Jan. 1998, vol. 61(1), Medical Economics Company, Inc., Montvale, NJ, USA, 20-24.
Mercier, et al., "Poly(lactide-co-glycolide) microspheres as a moldable scaffold for Cartilage Tissue Engineering", Biomaterials, vol. 26, 2005, 1945-1952.
Meyer, et al., "A New Abdominal Drain for Overflowing Lavage in Instances of Severe Pancreatitis with Persistent Peritoneal Contamination", Surgery, Gynecology & Obstetrics, vol. 165, Sep. 1987.
Meyer, et al., "Selections from Bier's Hyperemic Treatment in Surgery, Medicine, and the Specialties: A Manual of Its Practical Application", W.B. Sunders Co., 2 Ed., 1909, 17-25, 44-64, 90-96, 167-170, and 210-211.
Mikos, et al., "Preparation of Poly(glycolic acid) Bonded Fiber Structures for Cell Attachment and Transplantation", Journal of Biomedical Materials Research, vol. 27, 1993, 183-189.
Miyauchi, et al., "Repair of Incisional Hernia with Prolene Hernia System", The Journal of Medical Investigation, vol. 50, p. 108-111, 2003.
"Algorithm for Abdominal Wall Construction", Plastic and Reconstructive Surgery, Jan. 2000, 207-209.
"All Silicone Jackson Pratt Style Flat Drain", C. Daniel Medical, Inc., retrieved from internet Mar. 15, 2007, http://www.cdanielmedical.com/flat-drain.html, 1-2.
"All Silicone Jackson Pratt Style Round Drain", C. Daniel Medical, Inc., retrieved from internet Mar. 15, 2007, http://www.cdanielmedical.com/round-drain.html, 1-2.
"Antibacterial Silver Wound Dressing, Bandage, Gauze and Adhesive Strips", Silverlon Woundcare Products; http://www.silverlon.com/wound.htm; retrieved from Internet Jul. 27, 2006, 1-5.
"Hydrophobic Rigid Canisters", http://www.bemishealthcare.com/docs/anisterHydrophobic; Retrieved from Internet Mar. 15, 2007, 1-1.
"International Preliminary Examination Report and Search Report", PCT/GB96/02802, Jan. 15, 1998 and Apr. 29, 1997.
"International Search Report", PCT/GB98/02713, Jan. 8, 1999.
"International Search Report", PCT/GB95/01983, Nov. 23, 1995.
"International Search Report and Written Opinion", PCT/US2013/069756, Jan. 30, 2014, 1-10.
"NPD 1000 Negative Pressure Wound Therapy System", Kalypto Medical: www.kalyptomedical.com, Sep. 2008, 1-4.
"Occlude", Merriam-Webster Online Dictionary; http://www.merriam-webstercom/dictionary/occlude; retrieved from Internet Mar. 4, 2008.
"Patentee's Observations on the Oppositions", KCI Licensing, Inc. Response to Opponents Smith & Nephew, Inc., and Paul Hartmann Aktiengesellschaft Oppositions, Apr. 21, 2011, 1-15.
"PCT Written Opinion", PCT/GB98/02713, Jun. 8, 1999.
"PCT Written Opinion", PCT/GB96/028202, Sep. 3, 1997.
"Search Report and Written Opinion of the International Search Authority", International Application No. PCT/US06/38855 filed Oct. 3, 2006, report issued Aug. 8, 2007.
"Smith & Nephew, Inc. Opposition against EP 1,513,478", Sep. 16, 2010.
"Specific Dressing Techniques and Specialty Dressings", 25.
"V.A.C. Therapy Clinical Guidelines: A Reference Source for Clinicians", Jul. 2007.
Aktiengesellschaft, "Opposition to EP1513478", Sep. 16, 2010.
Ambrosio, et al., "V.A.C. GranuFoam Silver Dressing a New Antimicrobial Silver Foam Dressing Specifically Engineered for Use with V.A.C. Therapy", http://silverlon.com/fda.html, retrieved from the Internet Jul. 27, 2006, 1-71.
Anderson, et al., "Design of Tissue Engineering Scaffolds as Delivery Devices for Mechanical and Mechanically Modulated Signals", Tissue Engineering, vol. 13, No. 10, 2007, 2525-2539.
Arcand, et al., "Negative Pressure Wound Therapy and Its Application to Orthopaedics. Part II: Clinical Application", Osteo Trauma Care, 2006, 254-258.
Argenta, et al., "Vacuum-Assisted Closure: A New Method for Wound Control and Treatment: Clinical Experience", Annals of Plastic Surgery, vol. 38, No. 6, Jun. 1997, 563-576.
Armstrong, et al., "Planter Pressure Changes Using a Novel Negative Pressure Wound Therapy Technique", Journal of the Am. Podiatric Med. Assoc., vol. 94, No. 5, Sep. 2004, 456-460.
Arnljots, et al., "Irrigation Treatment in Split-Thickness Skin Grafting of Intractable Leg Ulcers", Scand J. Plast. Reconstr. Surg., 19, Nov. 19, 1984, 211-213.
Bagautdinov, "Variant of External Aspiration in the Treatment of Purulent Diseases of Soft Tissues", Ministry of Higher and Secondary Education of the RSFSR I.N Ulyanov Chuvash State University, 1986, 94-96.
Baig, et al., "Percutaneous Postoperative Intra-Abdominal Abscess Drainage After Elective Colorectal Surgery", Tech Coloproctol, vol. 6, 2002, 159-164.
Barker, et al., "Vacuum Pack Technique of Temporary Abdominal Closure: A 7-Year Experience with 112 Patients", The Journal Trauma: Injury, Infection and Critical Care, vol. 48, No. 2, Feb. 2000, 201-207.

* cited by examiner

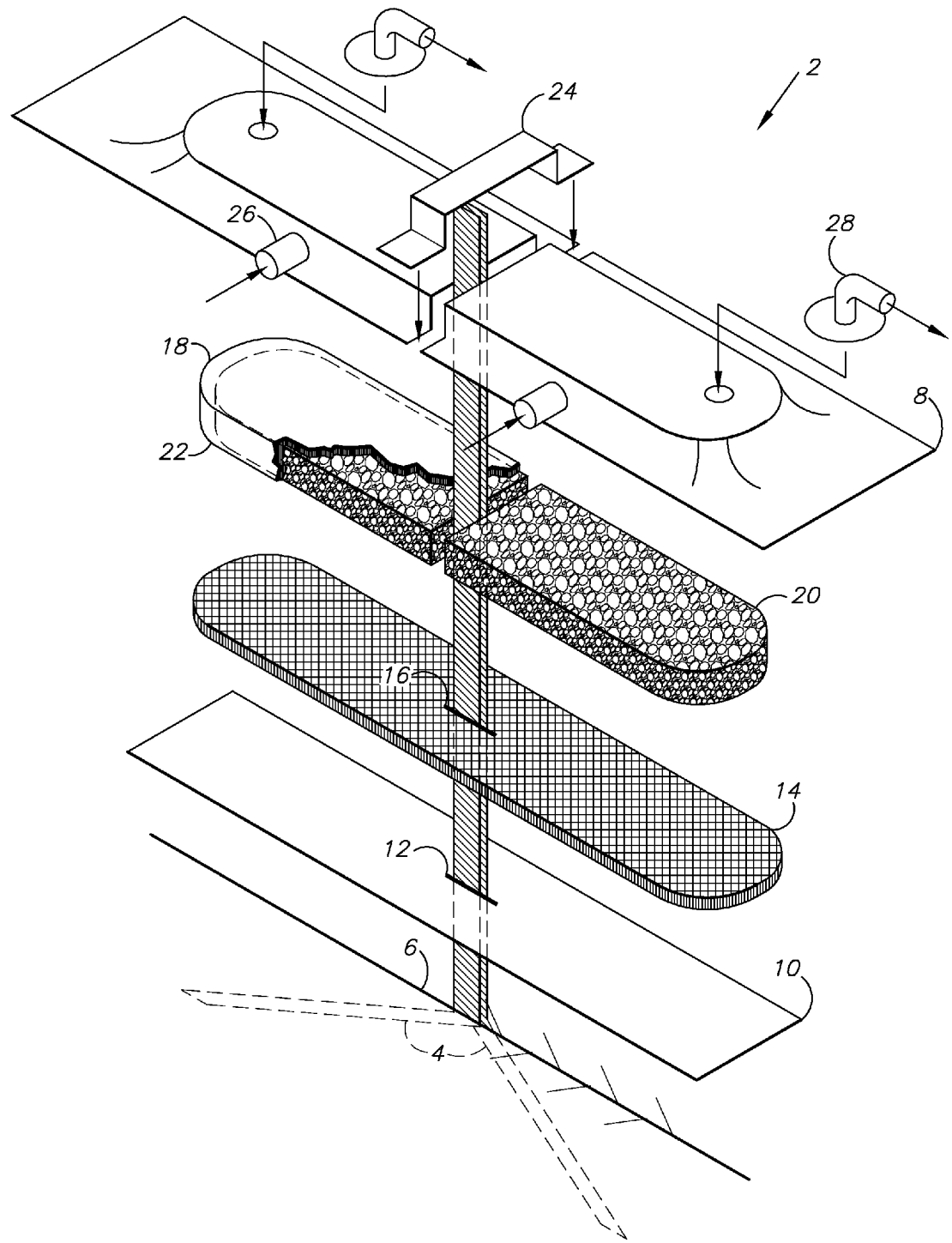

TOPICAL VACUUM-PRESS SURGICAL INCISIONAL DRESSINGS, SURGICAL ADJUNCTS, HYBRIDS AND COMPOSITES

CROSS-REFERENCE TO RELATED APPLICATION

This application claims priority in U.S. Provisional Patent Application Ser. No. 61/800,224, filed on Mar. 15, 2013, which is incorporated herein by reference. The following patents and published patent applications are related and are also incorporated herein by reference: U.S. Pat. No. 6,951,553, issued on Oct. 4, 2005; U.S. Pat. No. 6,936,037, issued on Aug. 30, 2005; U.S. Pat. No. 7,976,519, issued on Jul. 12, 2011; U.S. Publication No. 2011/0270201, published on Nov. 3, 2011, for U.S. patent application Ser. No. 13/181,399, filed on Jul. 12, 2011, U.S. patent application Ser. No. 13/245,677, filed on Sep. 26, 2011, and U.S. Provisional Patent Application Ser. No. 61/725,412, filed on Nov. 12, 2012.

BACKGROUND OF THE INVENTION

1. Field of the Invention

The present invention relates generally to negative pressure wound therapy (NPWT) and in particular to dressings for surgical incisions.

2. Description of the Related Art

Current external or topical vacuum-assisted dressings (also referred to as negative pressure wound therapy (NPWT) systems (e.g., post-surgical, incisional dressing systems)) have been shown to quickly (e.g., possibly within a few hours) seal and close the dermal-epidermal portion of the skin incision (side-to-side). This has the consequence (clearly evident in several clinical studies now) of preventing surface bacteria from entering the incisional space or the wound below and thus preventing incisional or surgical wound infection, particularly superficial infection.

An area of investigation relates to the "deep" sub-dermal effects of topical vacuum-press systems and treatment procedures. For example, an investigational topic relates to the prevention or reduction of the effects of seroma and hematoma. Another area of investigation concerns how far sub-dermal or deep in the incision/surgical wound is there an effect of the dressing on the surface.

Previous systems have used rayon-wrapped Granufoam dressing material (Kinetic Concepts, Inc. of San Antonio, Tex.) and NPWT techniques on the skin surface with a liner, routinely accompanied by large dissection space procedures with deep "Hemovac-type" drains brought out through separate stab wounds peripheral to the incision. Differences in the behavior of these drains have been observed clinically compared to the drainage characteristics known to occur without the external vacuum-assisted dressing, indicating that post-incisional dressings effected outcomes. Without this vacuum-press type surface dressing, these Hemovac-type drains would have a significant measureable amount of drainage over the first few days, then decreasing to what is considered an "irritation" level of drainage (10-20 cc's of clear yellow serum—i.e., no bleeding, just the amount of reactive drainage associated with the simple presence of this plastic tube in the tissue preventing complete apposition of the tissue by its presence).

The concept is that this amount of drainage would continue day after day as long as the tube was in place. But with a NPWT type of dressing in place, drainage during the first few post-incision days can be significantly decreased—essentially to irritation levels. In fact, oozing into the drain, after closure of the incision, has sometimes been observed to suddenly stop after the foam dressing is compressed with the drains placed deeply, e.g., at fascia level. So it was felt that deep bleeding ceased when the vacuum-press dressing was compressed using NPWT procedures. These observations suggest that vacuum-press post-operative dressings decrease hematoma and seroma formation.

As an incision is being closed, tissue voids, pockets, spaces and irregularities may prevent firm tissue-to-tissue apposition and create an actual "space." This is quickly filled by fluid—depending on the circumstances, this fluid consists of a spectrum from pure blood to pure extracellular and lymph fluid without any blood or serum clotting factors. The initial behavior of this fluid collection depends on which side of the spectrum it is. If there is enough pure blood to clot, this will be a hematoma. The consequence of any "space-occupying" hematoma is that the process of clot lysis, which proceeds over several days, carries with it the risk of "unclotting" blood vessels of sufficient size and pressure such that rebleeding occurs and causes a post-operative complication of an "expanding hematoma."

If re-bleeding does not occur, problems can occur with probable expansion at both ends of this spectrum of fluid in a space. Lysis, cell and clot breakdown with the freeing of protein can all produce particles that create an osmotic pressure. If this is greater than the absorptive capability, the fluid expands rather than contracts. If that occurs early before there is any collagen production with strength, then this breaks apart the surrounding tissue apposition (aided by any irregular tension from the suture position, necrosis from just the presence and nature of the suture ligatures, cautery debris, surface of the incision trauma from the very act of surgery, etc.). In other words, one can think of the dissection space of an operation as easier to be again split apart than to be held together.

So, even in a pure seroma that never had any blood in it to start with, there is still enough oncotic pressure from the unabsorbed large proteins such that expansion becomes a greater force than absorption and that, plus the simple mechanics of the presence of liquid between layers preventing collagen bridging and development of any strength between opposing layers of tissue, allows us to see that seromas also "expand" and we can see how just their very presence is a potentiating factor for "dehiscence."

If we look at the above scenarios, we get another glimpse at what NPWT-Incisional Dressings or topical vacuum pack dressings systems seem to be doing: they are changing the healing process during the critical first 48 hours of wound healing. Because the dressing enhances and enables tissue apposition, not only at the surface but also at levels beneath the dressing, it reduces and prevents the early increase in size of liquid-filled space lesions in incisions. But a review of the current data suggests that it does not take away a space-occupying fluid collection that is already there on completion of the closure before a NPWT-incisional dressing is applied on the operating table. Use of a buried suction drain such as a Hemovac drain should reduce this. But looking at these dynamics in this way suggests another alternative.

If we look at methods to decrease the presence of liquid-filled space-occupying lesions (i.e. hematoma/seroma) at the moment the incision is compressed on the operating table, we see an alternative to Hemovac drains brought out through a separate stab wound and left for several days, and to the option of preventing complete sealing of the incision by placing Swanson-type or wick drains through the incision, at its end or between sutures and leaving them for 24 to 72 hours to allow the incision to drain, and then having to change the entire topical vacuum-pack system, and that alternative is to drain the hematoma/seroma collections that form during closure on the operating table just before or, preferably, just after the foam core in the external dressing is compressed and then remove the drain and seal the dressing before the patient leaves the operating MOM.

Again, this entire concept can be summarized by the idea of the "set" of the wound or incision. Orthopedic surgeons reduce and hold fractures in position as the plaster cast is applied. Plastic surgeons roll and "milk" wounds to get everything drained and in a suspended new position before the wrap or tape or garment is applied to hold this "set." General surgeons use "retention" sutures and large ligatures to hold at-risk abdominal incision closures in place.

External vacuum-assisted NPWT systems use dressings that are eminently suited to hold the tissues in set apposition. The task then is to formalize the final removal of still-present drainage and to arrange the set of the wound as the foam core compresses. This disclosure then is to propose alternative methods and materials to accomplish that for both the peel-and-place and the customizable NPWT systems.

SUMMARY OF THE INVENTION

In the practice of the present invention, topical, NPWT surgical incisional systems and methods are provided, which can include surgical adjuncts, hybrids and composites. Wound therapy can be utilized with these systems and methods for facilitating wound healing and reducing potential complications.

Other objects and advantages of the present invention will be apparent from the following description. Detailed descriptions of exemplary embodiments are provided in the following sections. However, the invention is not limited to such embodiments.

BRIEF DESCRIPTION OF THE DRAWINGS

The drawings constitute a part of this specification and include exemplary embodiments of the present invention illustrating various objects and features thereof.

FIG. 1 is an exploded diagram of a NPWT system applied to an incision.

DETAILED DESCRIPTION OF THE PREFERRED EMBODIMENTS

I. Introduction and Environment

As required, detailed aspects of the present invention are disclosed herein; however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, up, down, front, back, right and left refer to the invention as orientated in the view being referred to. The terms "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Embodiment 1—Percutaneous Drain Slip Peripheral to the Incision and to the NPWT System Can Be Placed "Outside" the Drape A NPWT system 2 is shown in FIG. 1 and includes percutaneous drain slips 4, which can extend into an incision 6 and terminate exteriorly at a film cover or drape 8. The slip drain 4 material can be any type of fluid impermeable thin plastic or rubber of small caliber (only a few millimeters in width) that will slide easily in the tissues and be of sufficient tensile strength that it will not tear or break as it is removed. Silicone wicks of the Swanson Drain variety are an example. They can be provided in the dressing kits or as a separate package in a roll or coil of 100 cms. This should be sufficient to run the entire length of the incision or cut into sections and run half the incision length—past either end or out the sides.

The slip drains 4 can be placed in the incision 6 and extend towards opposite ends and can exit the incision at an approximate midpoint and extend upwardly through appropriate openings or slits 12, 16 in a wick 10 and a mat 14. The slip drains 4 can extend further outwardly between the recoil transfer assembly halves 18 and terminate under the film cover or drape 8, or externally to the dressing 2. The recoil transfer assembly halves 18 can include open-cell (e.g., polyurethane) foam or sponge material cores 20 with fluid-permeable (e.g., membrane or fabric) covers 22.

An exterior connector bridge 24 is attached on the exterior of the drape 8 and can be used to cover a gap between drape sections. The dressing system 2 can thus be customized to various lengths and configurations. Fluid inlets 26 can be located in the sides of the dressing assembly 2 and fluid outlets comprising elbow-configuration fittings 28 can be placed on the top of the dressing system 2. Various fluid inlet and outlet configurations and placements can be utilized.

Alternative slip drain configurations could be utilized with different numbers of slip drains, wound interfaces and dressing exits. Moreover, various types of drain devices could be utilized and connected to external devices, including other dressings, as indicated for a particular incision or treatment procedure.

The technique would be to lay this strip at fascial level after its closure or in the depths of the wound or in specific planes that the surgeon feels are at risk for seroma/hematoma collection. The drain is brought from the inside to the outside through a percutaneous stab wound using a long narrow clamp from the inside and incising a tiny stab wound over the clamp tip holding it at skin level, re-grasping the drain from the outside and then pulling it through till it is flat or straight in the incision bed. Skin closure is completed and the external dressing with foam core and liner is applied and vacuum instituted. The wound is then massaged and manipulated side to side to insure all deep layers are in good apposition. The incision, over the NPWT-incisional dressing is then rolled from the point(s) furthest away from the percutaneous drain site toward it. The egress and collection of this drainage is enhanced by using the ubiquitously available operative suction at the percutaneous stab wound with a 4×4 gauze sponge over the drain (and under it if desired). The suction picks up the drainage as it egresses and enhances its migration outward. After the rolling (or even simple manual milking), the suction is kept in place over the 4×4 as the drain is pulled out beneath it. The skin stab wound is then sealed with a simple steri-strip or small piece of paper tape over it. The patient is then allowed to emerge from anesthesia and taken to recovery and the incisional NPWT continued as usual.

III. Embodiment 2—Drain Slip Brought Out Through the Incision or Percutaneously but Still "Inside" and Under the Drape and/or the Foam and Mat of the Dressing In this embodiment, the materials provided in the "drain" kit include the above described 100 cm roll of silicone slip drain (sizes and material specifics are NOT limiting) but also a convenient size of a covering wicking fabric (e.g. 3 or 4 pieces of rayon about ½ inch wide by 4 inches in length) and sealing strips (3 or 4 pieces of hydrocolloid about 8-10 mm's wide—such as are available in the new customized Prevena NPWT kit from Kinetic Concepts, Inc. to allow edge sealing) and strips of sealing drape.

The method is similar to that described in the first embodiment except that after laying the slip drain along the fascia, it is brought up to the surface at the end or edge of the incision (can theoretically be any point judged optimal by the surgeon to evacuate potential deep space collections of drainage). Closure is completed and the drain, from the incision to a point beyond where the drape will end, is covered with the protective wicking strips (e.g. rayon). The vacuum is then applied to the external dressing, the foam core compressed and the rolling/milking and drainage evacuating procedure described above is carried out, again protecting and enhancing the evacuation point with a 4×4 gauze sponge and using the operating-room suction. The drain slip is aided in its removal under the drape by the presence of the intervening wick material which is left in place and the edge, where the drain was removed, of the wicking material beyond the drape is trimmed and the potentially open leak point of the wicking material exit site is sealed by applying a hydrocolloid strip and additional drape over this point.

An adjunctive maneuver that may aid the application of compression to the external dressing foam over the incision before the drain is extracted (as described above), now that we have, as it were, a built-in significant leak where we've run the drain slip under the drape, is to use the operative suction to draw down the foam (avoiding exhausting the battery life of the small vacuum pump), digitally pressing down on the drain-slip area to decrease the leak, and then clamping the tubing to the attachment patch on the dressing (rubber-shod clamp or similar method). The operative suction is then available to place on the drain exit point and proceed as described above. After the drain is removed and the edge sealed, the vacuum pump can be applied to the tubing and the procedure is completed. Of course, this step is not necessary if there are two suction sources in the OR or if one source is split with a Y-tube. So these are additional options.

It should be understood that there are many varieties and alternatives of applying these principles of draining the fluid and achieving the "set" of the operative wound—before or after the vacuum pack system is applied or compressed. The classic Swanson drain technique is to close the incision first and then use long, thin forceps to inset the drain slip between the sutures. Doing this, we can see that one option is even to just cover the drain slips with 4×4 gauzes or a lap tape and manually form and mold and compress the wound to get the residual drainage out and the remove the slips and apply the external vacuum dressing. The drain slips can be brought out at any area of the incision or, as described above, percutaneously beyond the incision. These maneuvers reduce the risk of spaces where tissue is not apposed, which will subsequently become seromas and hematomas. Because of this reduced risk, the need for a Hemovac-type drain is reduced.

It is to be understood that the invention can be embodied in various forms, and is not to be limited to the examples discussed above. The range of components and configurations which can be utilized in the practice of the present invention is virtually unlimited.

Having thus described the invention, what is claimed as new and desired to be secured by Letters Patent is:

1. A negative pressure wound therapy (NPWT) dressing configured for application to a skin surface over an incision and configured for connection to a negative pressure source, which dressing comprises:
    a fluid-permeable wick element configured for placement over the incision;
    a fluid transfer component configured for placement on the wick element and including an exterior surface;
    said transfer component configured for connection to the negative pressure source and for transferring fluid from the incision through the wick element and to the exterior surface;
    said transfer component configured for transmitting negative pressure from the negative pressure source to the incision;
    a drape placed over the transfer component and adapted for releasable connection to a skin surface around the incision;
    a slip drain comprising a fluid-impermeable material and having a proximal end adapted for placement in the incision and a distal end communicating with the negative pressure source; and
    gaps in said wick element and said transfer component configured for allowing said slip drain through to the surface.

2. The NPWT dressing according to claim 1, which includes:
    said slip drain comprising a pair of material strips each having proximal ends placed in the incision and distal ends adapted for communicating with the negative pressure source; and
    said slip drain configured for extending through the wick element and the fluid transfer component.

3. The NPWT dressing according to claim 1, which includes:
    a permeable material mat placed between the wick element and the transfer component and adapted for transferring fluid therebetween; and
    aligned slits in said wick element and said mat and slidably receiving said material strips.

4. The NPWT dressing according to claim 2, which includes:
    said material strip proximal ends being configured for placement in spaced relation within the incision; and
    said material strips generally being respectively adjacent to each other distally from said proximal ends.

5. The NPWT dressing according to claim 1, which includes:
    said transfer component comprising first and second sections positioned adjacent to each other; and
    said slip drain extending between said transfer component sections.

6. The NPWT dressing according to claim 5, which includes:
   each said transfer component section having an elongated configuration with a first end and a second end;
   said transfer component section first ends being positioned in abutting relation to each other with said transfer component sections being configured for fluidic transfer therebetween; and
   said slip drain extending between said transfer component section first ends.

7. The NPWT dressing according to claim 6, which includes:
   said drape comprising first and second sections positioned over said first and second transfer component sections respectively.

8. The NPWT dressing according to claim 7, which includes:
   a drape bridging strip placed over said transfer component section first ends and said drape sections for closing said drape and covering relation over said transfer component.

9. The NPWT dressing according to claim 7, which includes:
   an inlet fluid connection mounted on said drape and configured for introducing fluid to said transfer component; and
   an outlet fluid connection mounted on said drape and configured for extracting fluid from said transfer component.

10. The NPWT dressing according to claim 1, which includes:
    a component connected to the transfer component and configured for providing a cell manipulating factor source;
    an inflow line fluidically connecting the factor source to the transfer component; and
    an outflow line from the transfer component.

11. A negative pressure wound therapy (NPWT) dressing configured for application to a skin surface over an incision and configured for connection to a negative pressure source, which dressing comprises:
    a fluid-permeable wick element adapted for placement over the incision;
    a fluid transfer component configured for placement on the wick element and including an exterior surface;
    said transfer component configured for connection to the negative pressure source and for transferring fluid from the incision through the wick element and to the exterior surface;
    said transfer component configured for transmitting negative pressure from the negative pressure source to the incision;
    a drape placed over the transfer component and adapted for releasable connection to a skin surface around the incision;
    a slip drain comprising a fluid-impermeable material and having a proximal end adapted for placement in the incision and a distal end communicating with the negative pressure source; and
    said slip drain extending externally of said drape to said distal end.

12. The NPWT according to claim 11, which includes additional steps of:
    a fluid-permeable mat between the wick and the transfer component; and
    said dressing transferring fluid under negative pressure from the mat to the transfer component.

13. The NPWT dressing according to claim 12, which includes:
    said transfer component including a compressible, open-cell foam core.

14. The NPWT dressing according to claim 13, which includes:
    a permeable membrane flexible cover enclosing said transfer component core.

15. The NPWT dressing according to claim 11, which includes:
    said wound comprising an incision;
    drain tubing placed within said incision; and
    said drain tubing configured for extracting fluid from said incision.

16. The NPWT dressing according to claim 11, which includes:
    said dressing being configured for setting edges of said wound in apposition to each other; and
    said dressing being configured for drawing said wound edges together in abutting relation using NPWT applied via said transfer component.

17. The NPWT system according to claim 11, which includes:
    said transfer component including first and second sections;
    said dressing configured for placing said transfer component sections adjacent to each other; and
    said slip drain configured for extending between said transfer component sections.

18. The NPWT dressing according to claim 12, which includes:
    a wick slit in said wick;
    a mat slit in said mat; and
    said slip drain configured for extending through said wick and mat slits.

19. The NPWT dressing according to claim 18, which includes:
    said slip drain including a pair of material strips each having distal and proximal ends;
    said material strip distal ends configured for placing in said wound in spaced relation from each other; and
    said material strips configured for extending through said wick slit, said mat slit and transfer component.

20. A negative pressure wound therapy (NPWT) draining system configured for preventing liquid-filled space-occupying lesions in sub-dermal layers surrounding an incision, the system comprising:
    a fluid-impermeable slip drain configured for draining fluid from sub-dermal layers surrounding an incision;
    said fluid-impermeable slip drain having a proximal end configured for placement in a sub-dermal plane at risk for liquid-filled space-occupying lesions and a distal end configured for placement through said incision;
    a NPWT surface dressing including a fluid-permeable wick element configured for placement over said incision, fluid transfer component configured for placement on said wick element, a gap configured for allowing said slip drain through said wick and said fluid transfer component, and a drape configured for releasable connection to a skin surface around said incision;
    a negative pressure source configured for applying negative pressure to said NPWT surface dressing and said slip drain; and
    a drape bridging strip configured for placement over said gap in said NPWT dressing to seal said incision.

* * * * *

UNITED STATES PATENT AND TRADEMARK OFFICE
CERTIFICATE OF CORRECTION

PATENT NO. : 9,456,930 B2
APPLICATION NO. : 14/217219
DATED : October 4, 2016
INVENTOR(S) : David S. Zamierowski It is certified that error appears in the above-identified patent and that said Letters Patent is hereby corrected as shown below:

In the Specification

In Column 3, Line 8, please replace "MOM" with "room".

Signed and Sealed this
Twenty-sixth Day of June, 2018

Andrei Iancu
*Director of the United States Patent and Trademark Office*